(12) United States Patent
Lam et al.

(10) Patent No.: US 10,039,624 B2
(45) Date of Patent: Aug. 7, 2018

(54) DENTAL FLOSS DEVICE

(71) Applicant: ID Infinity Limited, Hong Kong (HK)

(72) Inventors: Wai Kwong Gordon Lam, Hong Kong (HK); Fung Ling Yuen, Hong Kong (HK)

(73) Assignee: ID Infinity Limited, Hong Kong (HK)

( * ) Notice: Subject to any disclaimer, the term of this patent is extended or adjusted under 35 U.S.C. 154(b) by 0 days.

(21) Appl. No.: 15/594,703

(22) Filed: May 15, 2017

(65) Prior Publication Data

US 2017/0245972 A1   Aug. 31, 2017

Related U.S. Application Data

(63) Continuation of application No. PCT/CN2015/088123, filed on Aug. 26, 2015.

(30) Foreign Application Priority Data

Nov. 14, 2014   (HK) .................................. 14111572

(51) Int. Cl.
*A61C 15/00* (2006.01)
*A61C 15/04* (2006.01)

(52) U.S. Cl.
CPC .................................. *A61C 15/046* (2013.01)

(58) Field of Classification Search
CPC .............................. A61C 15/04; A61C 15/046
See application file for complete search history.

(56) References Cited

U.S. PATENT DOCUMENTS

| 4,214,598 A | 7/1980 | Lee |
| 4,832,062 A | 5/1989 | Grollimund et al. |
| 5,085,236 A | 2/1992 | Odneal et al. |
| 5,094,256 A | 3/1992 | Barth |
| 5,782,250 A | 7/1998 | Harrah, Jr. |
| 5,947,133 A | 9/1999 | Kossak |
| 8,387,629 B1 * | 3/2013 | Borg .................... A61C 15/043 132/325 |
| 2007/0204879 A1 | 9/2007 | Chen et al. |
| 2013/0333720 A1 * | 12/2013 | Gordon ................ A61C 15/046 132/323 |

FOREIGN PATENT DOCUMENTS

| CN | 1146323 A | 4/1997 |
| CN | 2368477 Y | 3/2000 |
| CN | 1748657 A | 3/2006 |
| CN | 201108510 Y | 9/2008 |
| CN | 101884568 A | 11/2010 |
| CN | 203468777 U | 3/2014 |
| CN | 103815976 A | 5/2014 |

(Continued)

OTHER PUBLICATIONS

International Search Report of PCT Patent Application No. PCT/CN2015/088123 dated Dec. 1, 2015.

(Continued)

*Primary Examiner* — Rachel Steitz (57) ABSTRACT

The present patent application relates to a dental floss device which includes a floss holder and a floss tensioner. The floss holder is used for holding a dental floss, and the floss tensioner is connected with the floss holder and is used for tensioning the dental floss held by the floss holder.

6 Claims, 11 Drawing Sheets

(56) References Cited

FOREIGN PATENT DOCUMENTS

| GB | 2160106 A | 12/1985 |
|---|---|---|
| GB | 2272161 A | 5/1994 |
| JP | 2001170083 A | 6/2001 |
| WO | 9422391 A1 | 10/1994 |

OTHER PUBLICATIONS

Search Report of Hong Kong Short-term Patent Application No. 14111572.7 dated Jan. 23, 2015.
Partial Search Report of counterpart European Patent Application No. 15858758.4 dated Nov. 9, 2017.
Supplementary European Search Report of counterpart European Patent Application No. 15858758.4 dated Mar. 7, 2018.

* cited by examiner

DENTAL FLOSS DEVICE

CROSS REFERENCE TO RELATED APPLICATIONS

The present application is a Continuation Application of PCT application No. PCT/CN2015/088123 filed on Aug. 26, 2015, which claims the benefit of Hong Kong Patent Application No. 14111572.7 filed on Nov. 14, 2014. All the above are hereby incorporated by reference.

FIELD OF THE TECHNOLOGY

This patent application relates to an oral cleaning tool, and in particular to a dental floss device.

BACKGROUND

A dental floss can be used to clean teeth. However, a user using a dental floss will face a number of problems, such as difficult operation, hand pain, inconvenience, unsightly and unsanitary. At present, dental flossers purchased from market are for one-time use. The use of these disposable dental flossers leads to wastage, environmental pollution, and so on. The current dental flosser provides only one dental floss. It does not meet the requirement of people having different teeth positions and teeth arrangements. The current dental flossers are easy to become loose, making cleaning of teeth and deposit on gum not satisfactory. Furthermore, it is difficult to effectively remove dental plaque.

SUMMARY

The technical problem to be solved is to provide a dental floss to alleviate the drawbacks of the prior art. The technical scheme for solving the technical problem is to provide a dental floss device, which may include a floss holder and a floss tensioner, the floss holder being used for holding a dental floss, and the floss tensioner being connected with the floss holder and used for tensioning the dental floss held by the floss holder.

The floss holder may include a head portion and a holding portion, the head portion being located at one end of the holding portion.

The holding portion may be provided with two floss-winding posts for holding and securing the dental floss.

The head portion may include a first arm portion, a second arm portion, a third arm portion, and a fourth arm portion, and an end of each of the first arm portion, the second arm portion, the third arm portion, and the fourth arm being formed with a clamping groove.

An angle between the first arm portion and the second arm portion is 70-85 degrees, an angle between the first arm portion and the holding portion is 125-140 degrees, an angle between the second arm portion and the holding portion is 125-140 degrees, an angle between the third arm portion and the holding portion is 80-95 degrees, an angle between the fourth arm portion and the holding portion is 80-95 degrees, and the third arm portion and the fourth arm portion are bent backwards by 23-38 degrees.

The dental floss device may further include a positioner for keeping the dental floss in position on the head portion.

In one embodiment, the head portion and the holding portion may be rotatable relative to each other, whereby the floss tensioner adjusts tension of the dental floss by adjusting rotation of the head portion relative to the holding portion.

In one embodiment, the floss tensioner can be located on the holding portion, the floss tensioner being movable relative to the holding portion, whereby tension of the dental floss is adjusted through movement of the floss tensioner.

In one embodiment, the head portion can be provided with a first gear and the holding portion can be provided with a second gear, the first gear and the second gear being engaged so that the head portion and the holding portion are rotatable relative to each other.

In one embodiment, the holding portion may be provided with a third gear, and the floss-winding posts being coupled with the third gear, whereby tension of the dental floss is adjusted through rotation of the floss-winding posts.

In one embodiment, the holding portion may be provided therein with a trough, the floss-winding posts being movable within the trough, whereby tension of the dental floss is adjusted through movement of the floss-winding posts.

The dental floss device disclosed in the present application has the following beneficial effects. The dental floss device can effectively and easily tension the floss by means of a floss tensioner. It can greatly enhance the cleaning effect on the teeth as well as gaps between the teeth. It can also effectively remove dental plaque.

The four arms of the dental floss device of the present application are arranged according to certain angles. These angles can be set to ensure formation of the best three-dimensional space so as to provide enough space to accommodate the teeth during operation of the dental floss. The dental floss device can be used at multiple angles within the mouth cavity. It is suitable for people having different positions and arrangements of teeth. The dental floss device allows users to easily clean the teeth and comfortably clean the teeth located at different positions.

BRIEF DESCRIPTION OF THE DRAWINGS

The dental floss device of the present application will be further described below with reference to the accompanying drawings wherein.

DETAILED DESCRIPTION

For a clearer understanding of the technical features, objects and effects of the dental floss device of the present application, specific embodiments will now be described in detail with reference to the accompanying drawings.

As shown in FIGS. 1 to 9C, a dental floss device may include a floss holder and a floss tensioner. The floss holder can be used for holding a dental floss. The floss tensioner can be connected with the floss holder and can be used for tensioning the dental floss held by the floss holder. The dental floss device of the present application can effectively and easily tension the dental floss. It can produce a tension force that is not achievable by simply pulling by bare hands. It can greatly enhance the cleaning effect on the teeth and gum. It can also effectively remove dental plaque.

Figure 1:
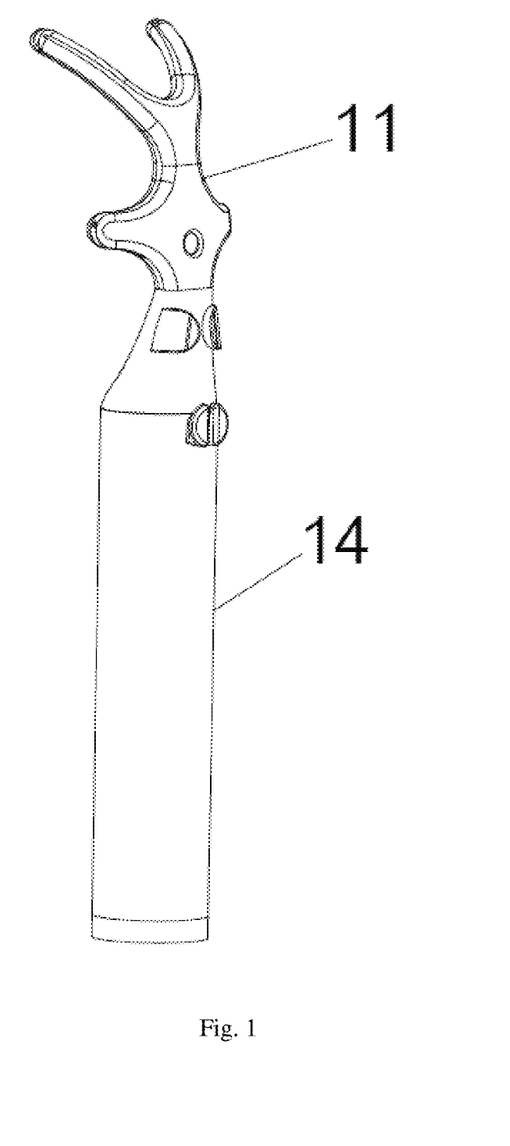
FIG. 1 is a schematic view of the structure of the dental floss device according to a first embodiment of the present application.
Figure 2A:
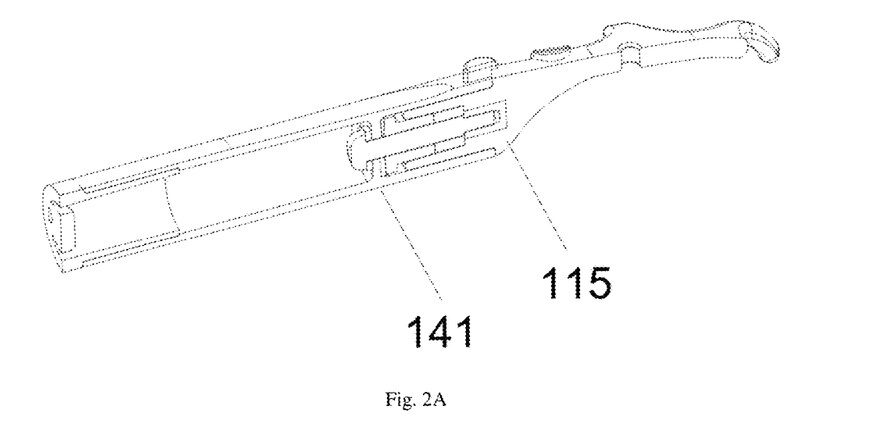
FIG. 2A is a schematic cross-sectional view of the dental floss device according to the first embodiment of the present invention.
Figure 2B:
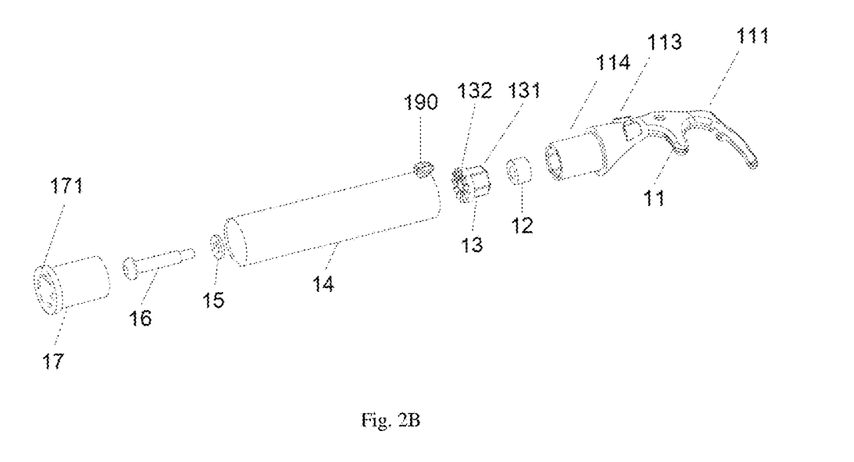
FIG. 2B is a schematic exploded view of the dental floss device according to the first embodiment of the present application.
Figure 3A:
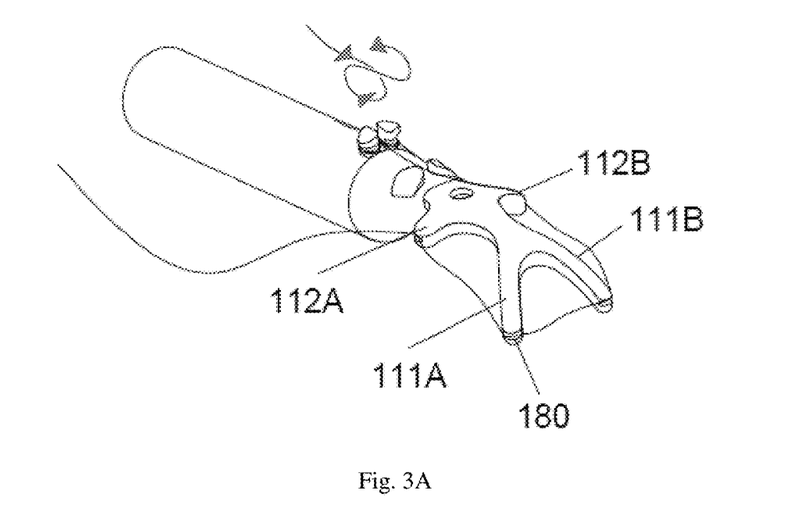
FIGS. 3A-3C are schematic views showing the operating condition of the dental floss device according to the first embodiment of the present application.
Figure 3B:
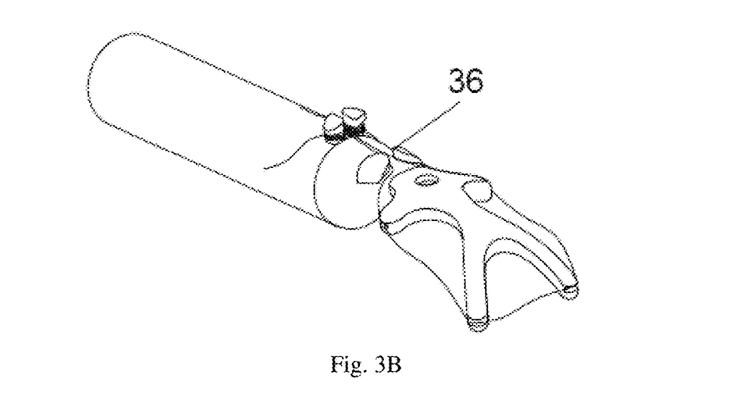
Figure 3C:
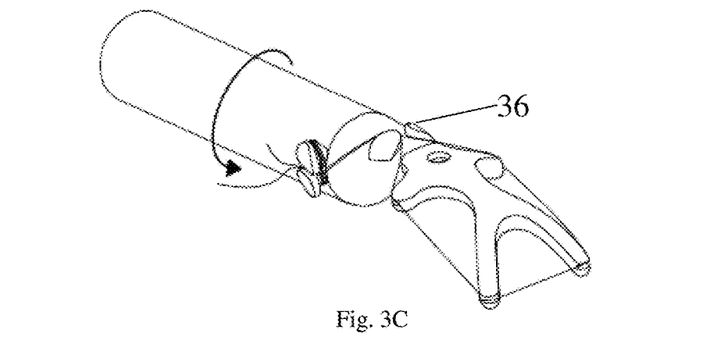

FIG. 1 is a schematic view of a first embodiment of the dental floss device of the present application. FIG. 2A is a schematic cross-sectional view of the dental floss device according to the first embodiment of the present invention. FIG. 2B is a schematic exploded view of the dental floss device according to the first embodiment of the present application. FIGS. 3A-3C are schematic views showing the operating condition of the dental floss device according to the first embodiment of the present application. FIGS. 4A-4D show the preferred angle settings for the dental floss device according to the first embodiment of the present application. FIGS. 5A-B show schematic views of the dental floss device in contact with the teeth according to the first embodiment of the present application.

As shown in FIG. 1, the floss holder may include a head portion 11 and a holding portion 14. The head portion 11 may be located at one end of the holding portion 14. The head portion 11 may bend upwards from the holding portion 14.

The bending shape of the head portion 11 conforms to ergonomic design which makes a user feel comfortable. Using the dental floss device of the present application, a user does not need to put his/her fingers in the mouth cavity, making it more hygienic. The dental floss device of the present application is easy to use.

As shown in FIGS. 3A, 3B and 3C, the head portion 11 may have a first arm portion 111A, a second arm portion 111B, a third arm portion 112A and a fourth arm portion 112B. An end of each of the first arm portion 111A, second arm portion 111B, third arm portion 112A and fourth arm portion 112B may be formed with a clamping groove 180 for holding the dental floss.

The fourth arm portion 112B and the second arm portion 111B of the head portion 11 may form a first space for tensioning a first segment of the dental floss. The second arm portion 111B and the first arm portion 111A may form a second space for tensioning a second segment of the dental floss. The first arm portion 111A and the third arm portion 112A may form a third space for tensioning a third segment of the dental floss. This can form a three-dimensional assembly of three dental floss segments extending in different directions.

Figure 4A:
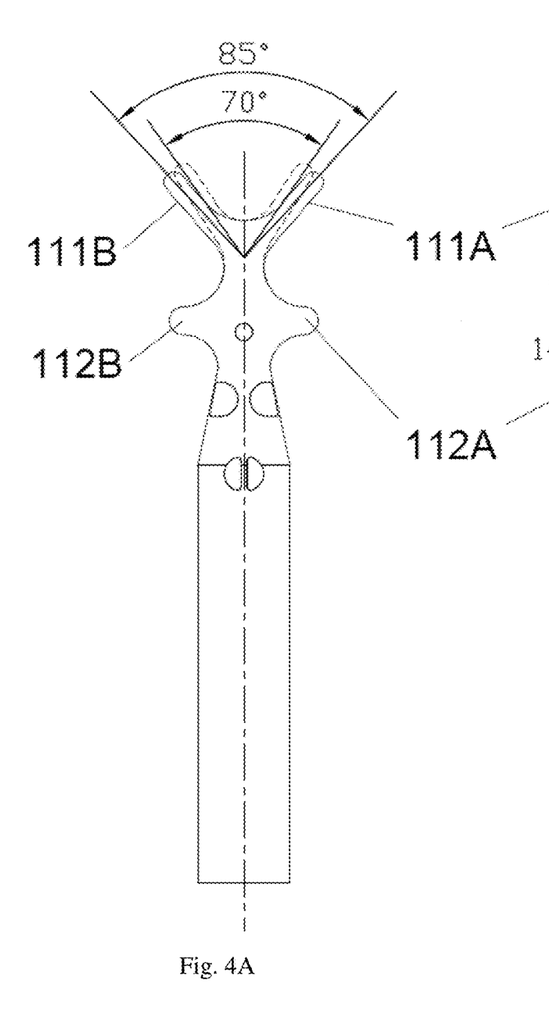
FIGS. 4A-4D show the preferred angle settings for the dental floss device according to the first embodiment of the present application.
Figure 4B:
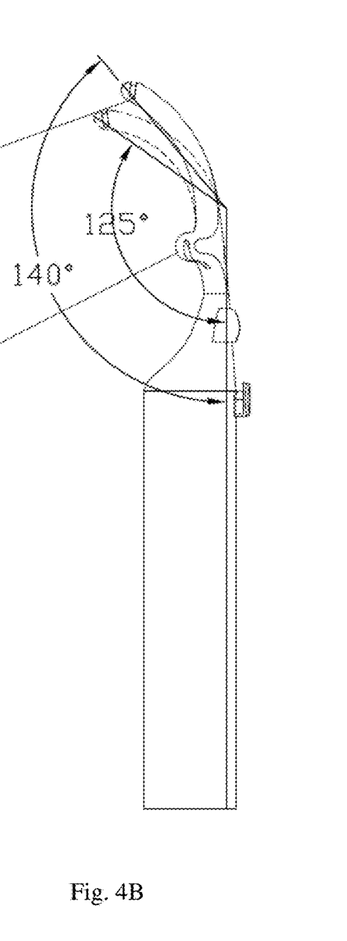
Figure 4C:
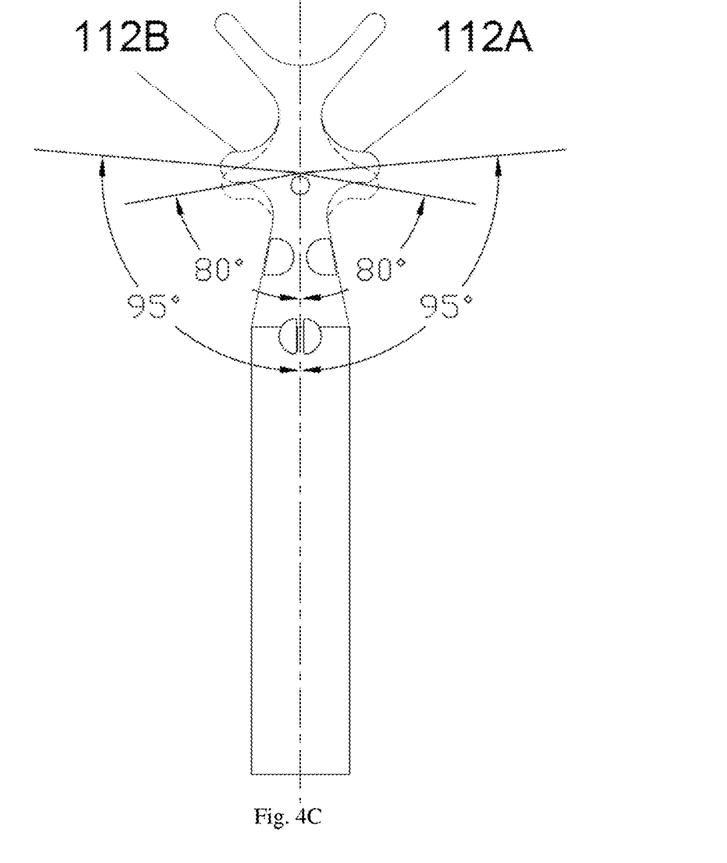
Figure 4D:
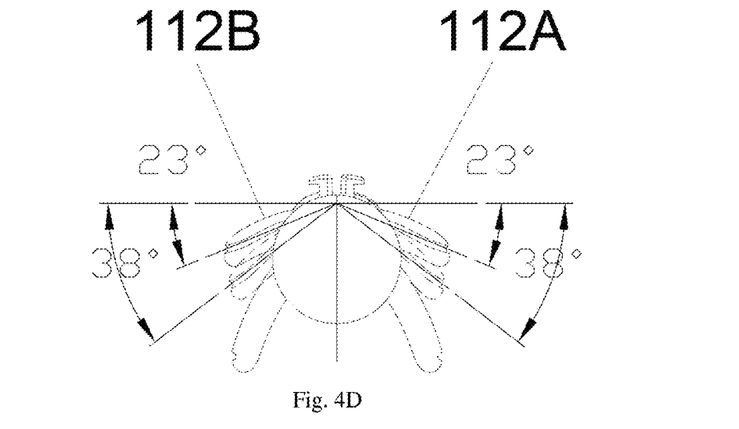
Figure 5A:
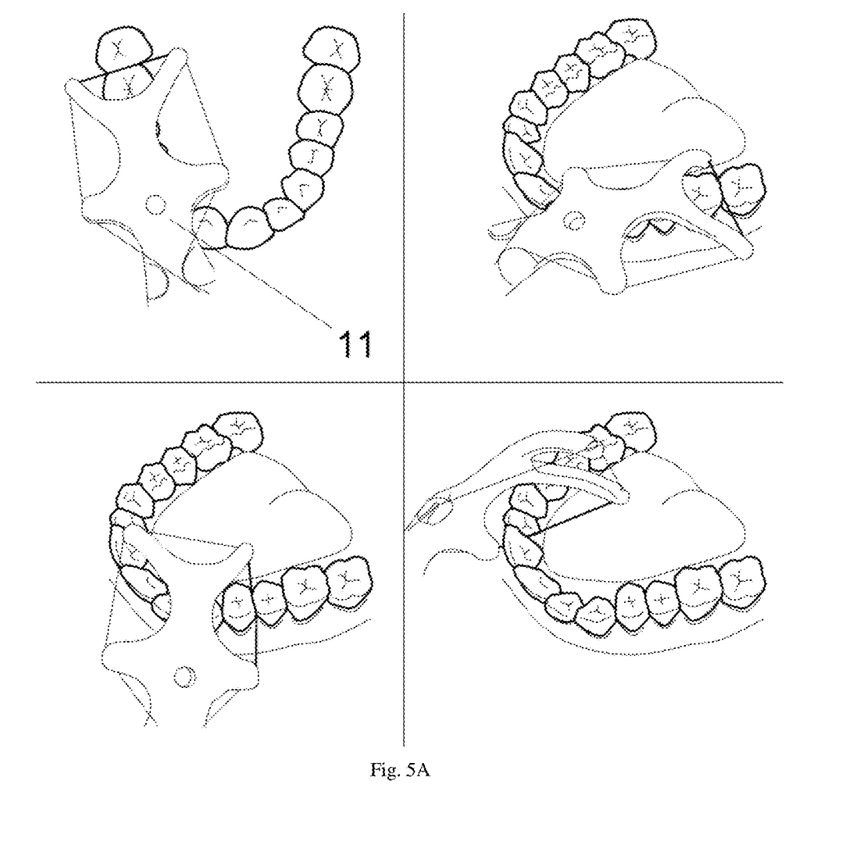
FIGS. 5A-B show schematic views of the dental floss device in contact with the teeth according to the first embodiment of the present application.
Figure 5B:
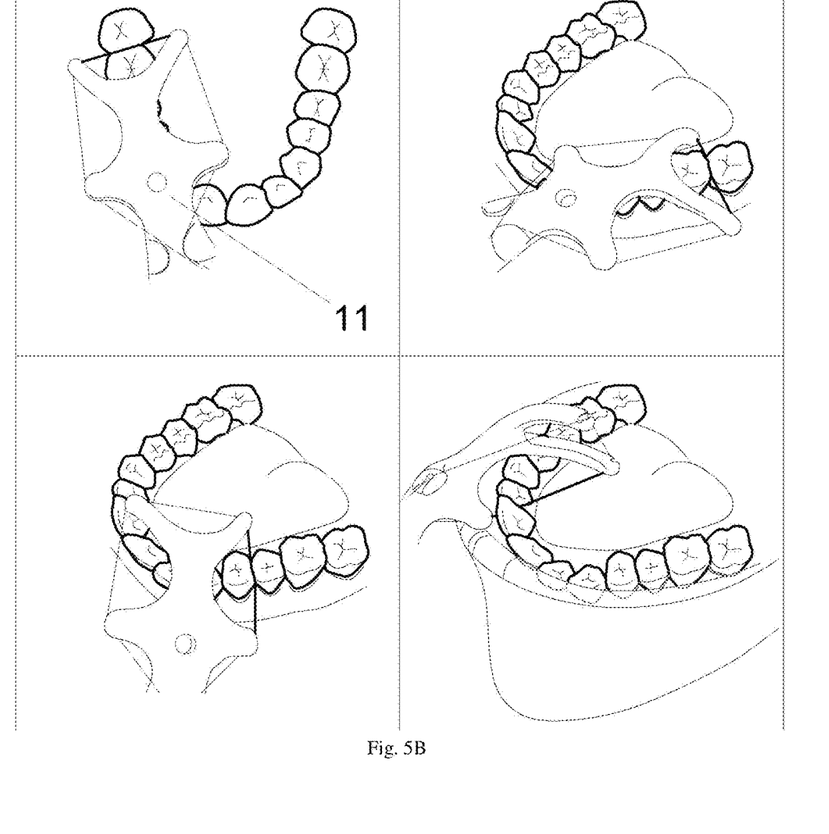

As shown in FIGS. 4A to 4D, the angle between the first arm portion 111A and the second arm portion 111B can be 70-85 degrees, the angle between the first arm portion 111A and the holding portion 14 can be 125-140 degrees, the angle between the second arm portion 111B and the holding portion 14 can be 125-140 degrees, the angle between the third arm portion 112A and the holding portion 14 can be 80-95 degrees, and the angle between the fourth arm portion 112B and the holding portion 14 can be 80-95 degrees. As shown in FIG. 4D, the third arm portion 112A and the fourth arm portion 112B may bend backwards by 23-38 degrees. As shown in FIGS. 5A-B, these angles can be set to ensure formation of the best three-dimensional space so as to provide enough space to accommodate the teeth during operation of the dental floss. The dental floss device can be used at multiple angles within the mouth cavity. It is suitable for people having different positions and arrangements of teeth. The dental floss device allows users to easily clean the teeth and comfortably clean the teeth located at different positions.

The head portion 11 and the holding portion 14 can be rotatable relative to each other. The floss tensioner can adjust the tension of the dental floss by adjusting rotation of the head portion 11 relative to the holding portion 14.

As shown in FIG. 3B, the lower half of the head portion 11 may be formed with a positioner 36 defined by two protrusions, which form a positioning gap 113. When the holding portion 14 is rotated, the protrusions 36 can effectively hold the dental floss in the middle of the head portion 11 to thereby assist in tensioning the dental floss and reduce swinging when the dental floss is being used.

As shown in FIGS. 2A and 2B, the floss tensioner may be provided inside the head portion 11 and the holding portion 14. Specifically, the bottom portion of the head portion 11 may be provided with a connecting cylinder 114 which can be connected to the holding portion 14. A polygonal space may be reserved in the connecting cylinder 114 for holding a first gear 13. The top portion of the first gear 13 can be in the form of a polygonal pillar 131 that engages in the polygonal space of the connecting cylinder 114. The bottom portion of the first gear 13 can be a one-way toothed wheel 132.

The holding portion 14 may be provided with floss-winding posts 190. The holding portion 14 may be cylindrical in shape and define a space in which a second gear 141 is located. The second gear 141 may engage with the first gear 13. The second gear 141 may also be one-way.

The space reserved within the connecting cylinder 114 may also be provided with an elastic ring 12. The elastic ring 12 can provide the required space for the rotation of the first gear 13 and the second gear 141, and can provide a braking action at rest. The top portion of the connecting cylinder 114 may be provided with a nut 115 for coupling with a screw 16 during assembly.

A circular hole may be provided in the center of the first gear 13, the elastic ring 12 and the second gear 141 through which the screw 16 can pass. The screw 16 in the holding portion can pass through a circular ring 15, the second gear 141, the first gear 13, the elastic ring 12, and can be fastened to the nut 115 so that the head portion 11 and the holding portion 14 can be fixed. The circular ring 15 can reduce frictional force when the holding portion 14 rotates so that rotation can be smoother.

The bottom portion of the holding portion 14 may be provided with a bottom cover 17 for covering the central hollow portion of the holding portion 14 in order to enhance appearance and hygiene. The bottom cover 17 may be provided with a water outlet 171 through which accumulated dirt can be washed out while cleaning the dental floss device.

As shown in FIGS. 3A-3C, when using the dental floss, about 30 cm of the dental floss is extracted. One end of the extracted dental floss is pressed against the holding portion by a thumb of one hand, and the other hand drives the dental floss in a floss-winding action. The dental floss is first passed through the gap between the two protruding floss-winding posts formed at the top portion of the holding portion, and then two loops are formed by winding the dental floss around the two floss-winding posts in the shape of the Arabic numeral "8".

The dental floss is then passed through the gap between the two positioning protrusions in the middle of the head portion. The dental floss is then placed in the clamping grooves 180 of the first arm portion 111A, the second arm portion 111B, the third arm portion 112A, and the fourth arm portion 112B of the head portion. Then, the dental floss is pulled back to the positioning gap and then down to the floss-winding posts 190 of the holding portion.

Then, two loops are again formed by winding the dental floss around the two floss-winding posts in the shape of the Arabic numeral "8". The remaining dental floss is tied onto the floss-winding posts.

To adjust the tension of the dental floss, the head portion 11 and the holding portion 14 are held by two hands respectively, and the holding portion 14 is rotated to the right until the dental floss at the head portion 11 reaches a sufficient tension. Since the holding portion 14 contains a one-way gear, the holding portion 14 does not retreat when it rotates, and the tension force of the dental floss is maintained.

As shown in FIGS. 5A-B, the head portion 11 is placed in the mouth cavity. The three dental floss segments extending in different directions can be used to clean the gap between teeth, gum and dental plaque. Since each person's teeth arrangement is different, the dental floss segments oriented in different directions can be used to suit individual comfort level. In general, it is recommended to use the left and right dental floss segments to clean the teeth at the front, such as the front teeth and the canines, and use the dental floss segment at the top of the head portion 11 to clean the molars deep inside the mouth cavity. A recess or concaved portion can be formed in a region below the first arm portion 111A and the fourth arm portion 112B of the head portion 11. When cleaning the lower row of teeth by the dental floss device, as shown in FIGS. 5A-B, the concaved portion can be held against the lip. This produces a buffer effect which can prevent the gum from being injured by the floss in case excess force is applied by a user at the time the floss is inserted into the gap between the teeth.

After cleaning of the teeth and gum is completed, the dental floss device is taken out and the dental floss is released from the dental floss device and is discarded. The dental floss device is then properly cleaned, disinfected, and placed in a cool and dry environment for storage.

The dental floss device of the present application consumes only about 30 cm of dental floss for each teeth cleaning. This is economical and environmental friendly.

Figure 6:
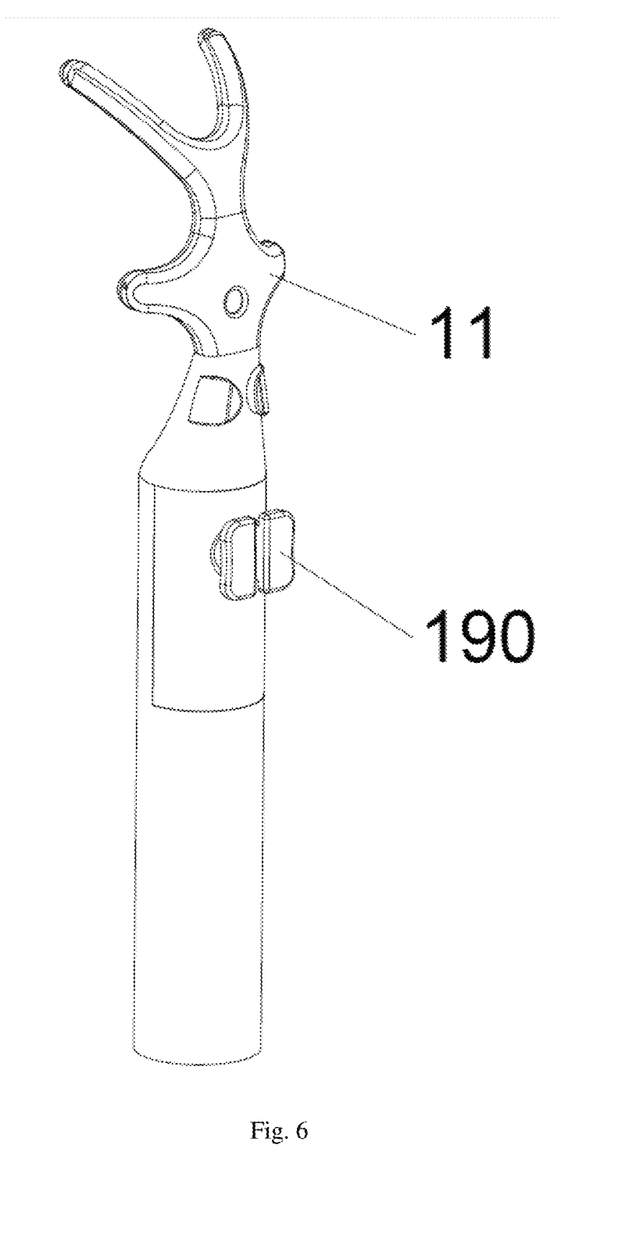
FIG. 6 is a schematic view of the structure of the dental floss device according to a second embodiment of the present application.
Figure 7:
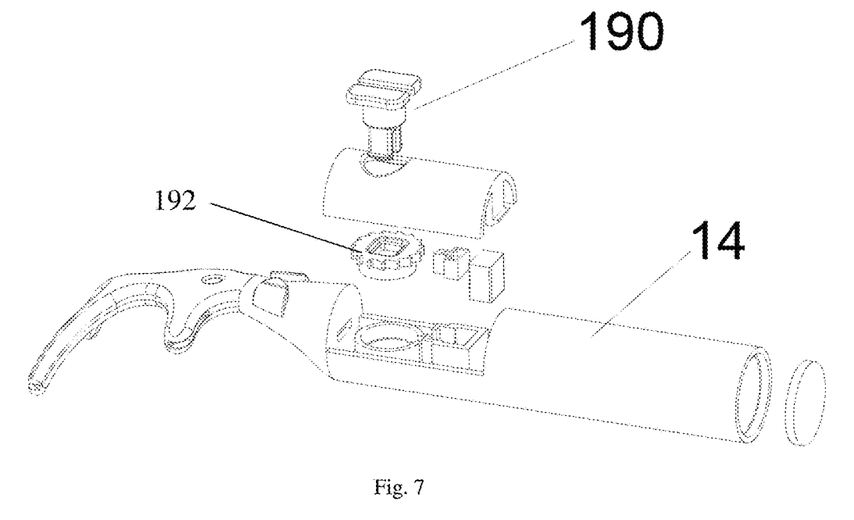
FIG. 7 is a schematic exploded view of the dental floss device according to the second embodiment of the present application.
Figure 8A:
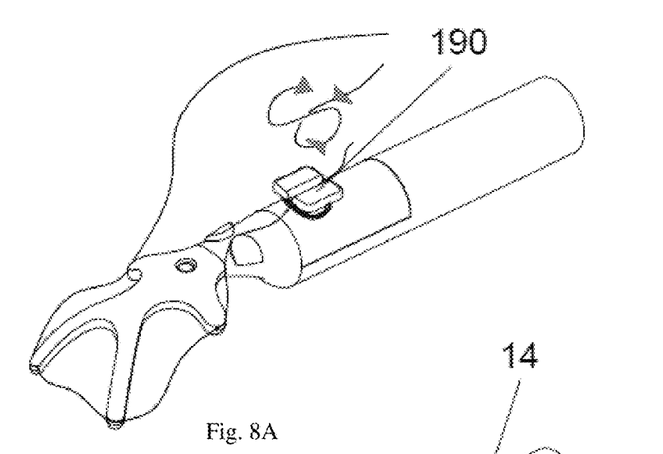
FIGS. 8A-8C are schematic views showing the operating condition of the dental floss device according to the second embodiment of the present application.
Figure 8B:
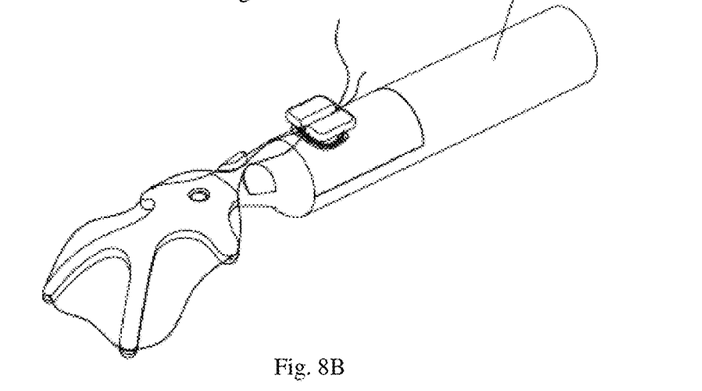
Figure 8C:
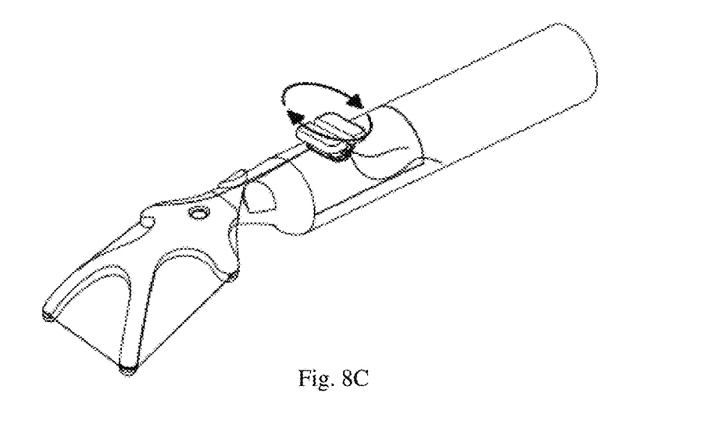

FIG. 6 is a schematic view of the structure of the dental floss device according to a second embodiment of the present application. FIG. 7 is a schematic exploded view of the dental floss device according to the second embodiment of the present application. FIGS. 8A-8C are schematic views showing the operating condition of the dental floss device according to the second embodiment of the present application.

As shown in FIGS. 6 to 8C, the floss tensioner can be located at the holding portion 14. The floss tensioner can be rotatable relative to the holding portion 14 to adjust the tension of the dental floss.

As shown in the embodiment shown in FIG. 7, the inside of the holding portion 14 is hollow in which a third gear 192 can be placed. The bottom portion of the floss-winding posts 190 can be coupled with the third gear 192. As shown in FIGS. 8A-8C, the tension of the dental floss can be adjusted by rotating the floss-winding posts 190.

Figure 9A:
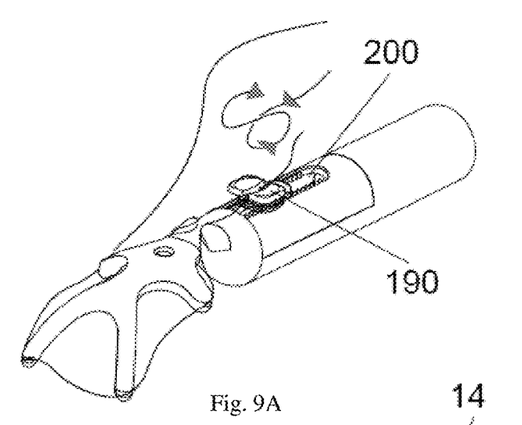
FIGS. 9A-9C are schematic views showing the operating condition of the dental floss device according to the third embodiment of the present application.
Figure 9B:
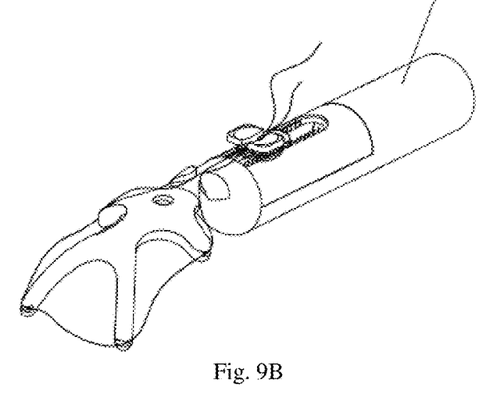
Figure 9C:
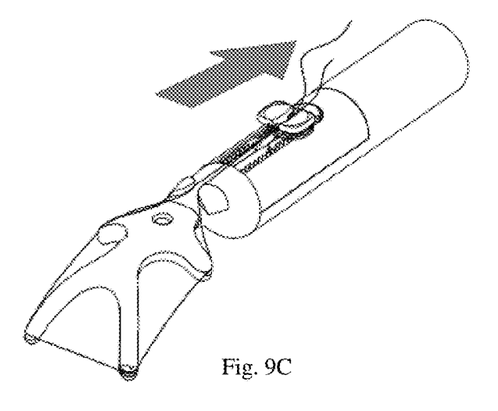

FIGS. 9A-9C are schematic views showing the operating condition of the dental floss device according to the third embodiment of the present application. As shown in FIGS. 9A-9C, the floss tensioner can be located at the holding portion 14. The floss tensioner can be movable relative to the holding portion 14 to adjust the tension of the dental floss.

In the present embodiment, a trough 200 may be provided in the holding portion 14. The floss-winding posts 190 can be moved within the trough 200. Further tensioning of the dental floss can be achieved by moving the floss-winding posts 190 from top to bottom along the trough 200.

The above three embodiments illustrate the floss tensioner only by way of examples. There can be many other forms of floss tensioner, as long as they can achieve adjustment of the tension of the dental floss.

Specific embodiments have been described above with reference to the accompanying drawings. However, the present application is not limited to the above specific embodiments. The above specific embodiments are merely illustrative and should not be considered as limiting. It should be noted that, upon reading the above disclosure, a person skilled in the art can make various other changes or modifications without departing from the scope of the appended claims.

What is claimed is:

1. A dental floss device, comprising a floss holder and a floss tensioner, the floss holder being used for holding a dental floss, and the floss tensioner being connected to the floss holder and used for tensioning the dental floss held by the floss holder, wherein the floss holder comprises a head portion and a holding portion, the head portion being located at one end of the holding portion, wherein the head portion and the holding portion are rotatable relative to each other, whereby the floss tensioner adjusts tension of the dental floss by adjusting rotation of the head portion relative to the holding portion, wherein the head portion is provided with a first gear and the holding portion is provided with a second gear, the first gear and the second gear being engaged so that the head portion and the holding portion are rotatable relative to each other, wherein the first gear comprises a one-way toothed wheel, wherein the second gear is one-way.

2. The dental floss device as claimed in claim 1, wherein the holding portion is provided with two floss-winding posts for holding and securing the dental floss.

3. The dental floss device as claimed in claim 2, wherein the head portion comprises a first arm portion, a second arm portion, a third arm portion, and a fourth arm portion, and an end of each of the first arm portion, the second arm portion, the third arm portion, and the fourth arm being formed with a clamping groove.

4. The dental floss device as claimed in claim 3, wherein an angle between the first arm portion and the second arm portion is 70-85 degrees, an angle between the first arm portion and the holding portion is 125-140 degrees, an angle between the second arm portion and the holding portion is 125-140 degrees, an angle between the third arm portion and the holding portion is 80-95 degrees, an angle between the fourth arm portion and the holding portion is 80-95 degrees, and the third arm portion and the fourth arm portion are bent backwards by 23-38 degrees.

5. The dental floss device as claimed in claim 1, further comprising a positioner for keeping the dental floss in position on the head portion.

6. The dental floss device as claimed in claim 1, wherein the head portion and the holding portion are rotatable relative to each other about an axis along a length of the holding portion, whereby the floss tensioner adjusts tension of the dental floss by adjusting rotation of the head portion relative to the holding portion.

* * * * *